United States Patent [19]
Bock et al.

[11] Patent Number: 5,834,464
[45] Date of Patent: Nov. 10, 1998

[54] IMIDAZOLINOBENZODIAZEPINES

[75] Inventors: Mark G. Bock; Robert M. DiPardo; Roger M. Freidinger, all of Rahway, N.J.

[73] Assignee: Merck & Co., Inc., Rahway, N.J.

[21] Appl. No.: 640,730

[22] PCT Filed: Nov. 18, 1994

[86] PCT No.: PCT/US94/13325

§ 371 Date: May 6, 1996

§ 102(e) Date: May 6, 1996

[87] PCT Pub. No.: WO95/14693

PCT Pub. Date: Jun. 1, 1995

[51] Int. Cl.$^6$ .................... A61K 31/395; C07D 487/04
[52] U.S. Cl. .................... 514/220; 540/559; 540/562
[58] Field of Search .................... 540/562, 559; 514/220

[56] References Cited

U.S. PATENT DOCUMENTS 4,847,248  7/1989  Freidinger .................... 514/214
5,439,906  8/1995  Bock et al. .................... 514/220

FOREIGN PATENT DOCUMENTS 0272866  6/1988  European Pat. Off. .

Primary Examiner—Mukund J. Shah
Assistant Examiner—Bruck Kifle
Attorney, Agent, or Firm—Sylvia A. Ayler; Mark R. Daniel

[57] ABSTRACT

Imidazolinobenzodiazepines are cholecystokinin B (CCK-B) antagonists useful as anxiolytic agents. The compounds have structures such as:

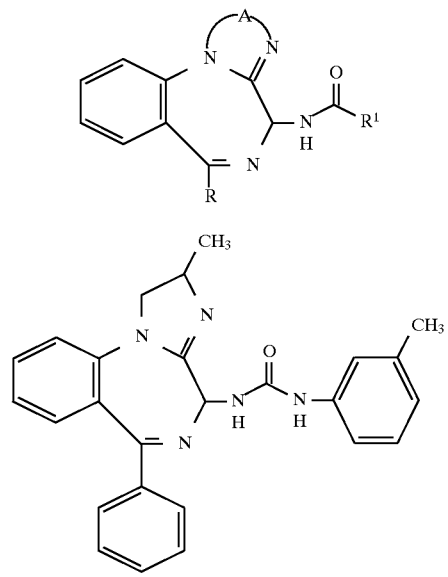

6 Claims, No Drawings

IMIDAZOLINOBENZODIAZEPINES

BACKGROUND OF THE INVENTION

The benzodiazepine class of compounds has been widely exploited as therapeutic agents, especially as central nervous system drugs, such as anxiolytics. They exhibit strong binding to "benzodiazepine receptors" and some exhibit binding to CCK-B or gastrin receptors. None of the compounds known to be a CCK-B antagonist is of the imidazolinobenzodiazepine type shown as structure I, below.

SUMMARY OF THE INVENTION

This invention is concerned with novel compounds of structure I:

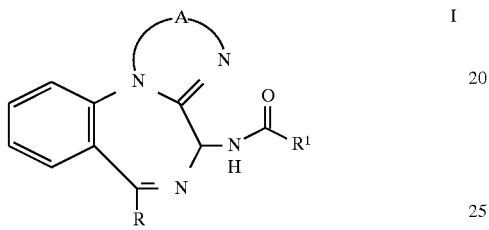

which are antagonists of CCK-B. They are useful in the treatment and prevention CCK-B related disorders of the central nervous systems of animals, preferably mammals and especially humans.

The invention is also concerned with pharmaceutical formulations of the novel compounds, processes for their preparation and the use of the novel compounds as anxiolytic agents.

DETAILED DESCRIPTION OF THE INVENTION

The novel compounds of this invention have structural formula:

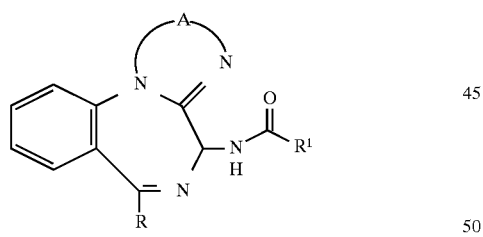

or a pharmaceutically acceptable salt thereof, wherein
R is
1) phenyl, either unsubstituted or substituted with halo, such as chloro, bromo or fluoro, or $C_{1-3}$ alkyl,
2) $C_{5-6}$ cycloalkyl;
A is
1) $C_{2-3}$ alkylene or alkenylene either unsubstituted or substituted with $C_{1-3}$ alkyl, hydroxy-$C_{1-3}$ alkyl, —COOH or $-\overset{O}{\underset{\|}{C}}-O\ (C_{1-3}\ alkyl)$; and $R^1$ is $-HN-\underset{\phantom{R^2}}{\text{(phenyl)}}-R^2$, wherein $R^2$ is chloro, $C_{1-3}$ alkyl, $C_{1-3}$ alkoxy or $-CF_3$, or

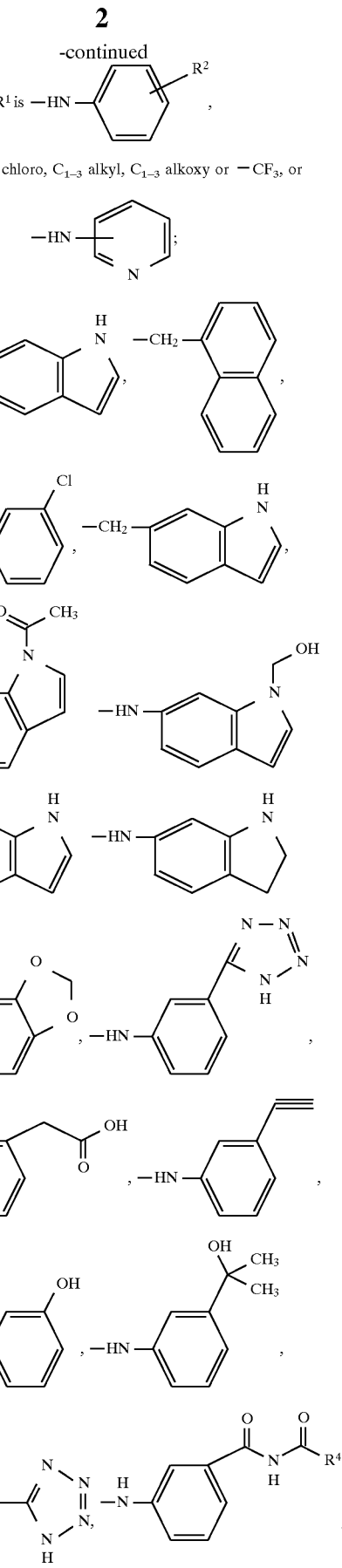

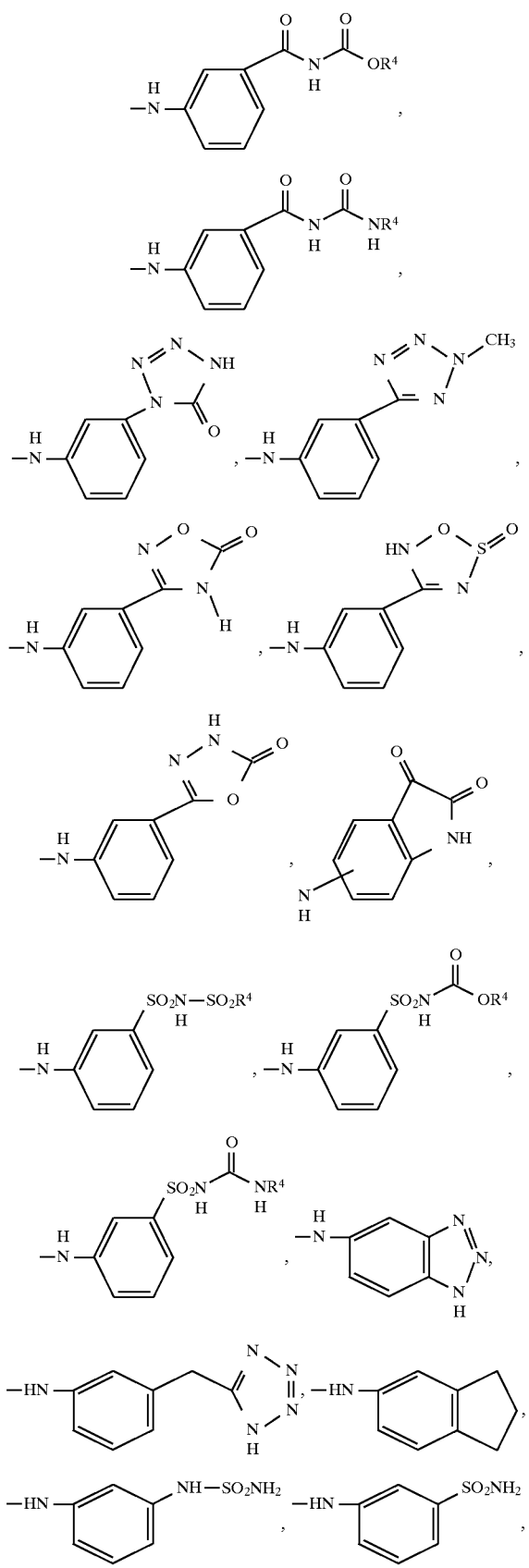

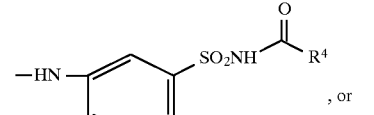, or

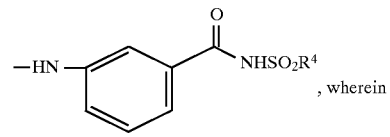, wherein

R⁴ is

C$_{1-6}$ alkyl, CF$_3$, cyclopropyl, 2,2-dimethylcyclopropyl, 2,2-di-fluorocyclopropyl, cyclobutyl, cyclopentyl, cyclohexyl, phenyl, or mono- or di-substituted phenyl wherein the substitution is C$_{1-3}$ alkyl, F, Cl, Br, CN, NO$_2$, CF$_3$, OCH$_3$, or NH$_2$.

One embodiment of the novel compounds of this invention is that wherein R$^1$ is

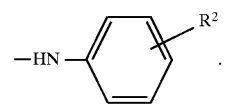

Specific compounds representative of this embodiment are those depicted in the following table:

| A | R | R² |
|---|---|---|
| —CH₂CH₂— | phenyl | 3-CH₃— |
| —CH₂—CH(CH₃)— | phenyl | 3-CH₃— |
| —CH₂—CH(CH₃)— | phenyl | 3-CH₃— |
| —CH₂—CH(CH₃)— | cyclohexyl | 3-CH₃— |
| —CH(CH₃)—CH₂— | phenyl | 3-CH₃— |
| —CH₂CH₂CH₂— | pheyl | 3-CH₃— |
| —CH₂—CH(CH₃)— | phenyl | 4-Cl— |
| —CH₂—CH(CH₃)— | phenyl | 3-Cl— |
| —CH₂—CH(CH₃)— | phenyl | 4-CF₃— |
| —CH₂—C(OH)— | phenyl | 3-CH₃— |
| —CH(OH)—CH₂— | phenyl | 3-CH₃— |

-continued

| A | R | R² |
|---|---|---|
| —CH—CH(—CH₃) | phenyl | 3-CH₃— |
| —CH—CH₂ (CH₃—) | phenyl | 3-CH₃— |
| —CH₂—C(H)(O)—OCH₃ | phenyl | 3-CH₃— |
| —CH=CH— | phenyl | 3-CH₃— |
| —CH—CH₂— (CH₃) | phenyl | 3-CH₃— |

This invention is meant to include the individual diastereomers where such exist and mixtures thereof and enantiomers and mixtures of the enantiomers.

The pharmaceutically acceptable salts of the compounds of Formulas I include the conventional non-toxic salts or the quarternary ammonium salts of the compounds of Formula I formed, e.g., from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the compounds of Formula I which contain a basic or acidic moiety by conventional chemical methods. Generally, the salts are prepared by reacting the free base or acid with stoichiometric amounts or with an excess of the desired salt-forming inorganic or organic acid or base in a suitable solvent or various combination of solvents.

The ability of the novel compounds to antagonize CCK-B makes these compounds useful as pharmaceutical agents for mammals, especially humans for the treatment and prevention of disorders wherein CCK-B is involved such as anxiety.

The compounds of Formula I may be administered to a human subject either alone or, preferably, in combination with pharmaceutically-acceptable carriers or diluents, optionally with known adjuvants, such as alum, in a pharmaceutical composition, according to standard pharmaceutical practice. The compounds can be administered orally or parenterally, including intravenous, intramuscular, intraperitoneal, subcutaneous and topical administration.

For oral use of an antagonist of CCK, according to this invention, the selected compounds may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

When a compound according to Formula I is used as an antagonist of CCK or gastrin in a human subject, the daily dosage will normally be determined by the prescribing physician with the dosage generally varying according to the age, weight, and response of the individual patient, as well as the severity of the patient's symptoms. However, in most instances, an effective daily dosage will be in the range of from about 0.05 mg/kg to about 50 mg/kg of body weight, and preferably, of from 0.5 mg/kg to about 20 mg/kg of body weight, administered in single or divided doses. In some cases, however, it may be necessary to use dosages outside these limits.

A novel process for preparing the novel compounds of this invention comprises treating a compound of formula II with a sulfonyl chloride such as methanesulfonyl chloride, benzenesulfonyl chloride or toluenesulfonyl chloride in an organic solvent methylene dichloride, chloroform, tetrachloroethane or the like in the presence of a strong organic base such as diisopropyl ethyl amine.

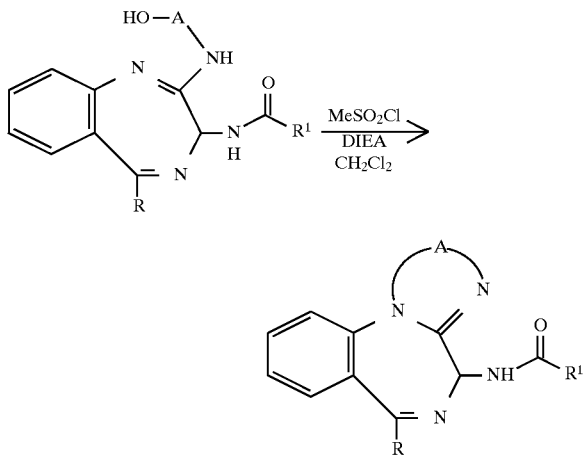

Another novel process for preparing some of the novel compounds of this invention is depicted as follows:

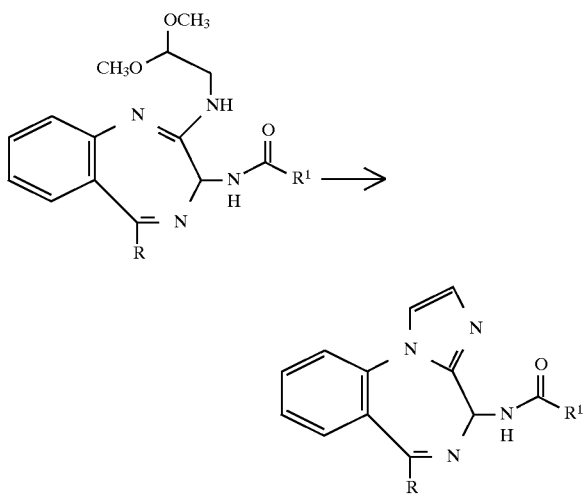

In this process, the hemiacetal starting material is treated with borontrifluoride etherate in a chlorinated alkane such as methylene chloride at about 40°–60° C. until the reaction is complete which occurs in about 1.5 to 3 hours.

A third novel process of this invention is depicted as:

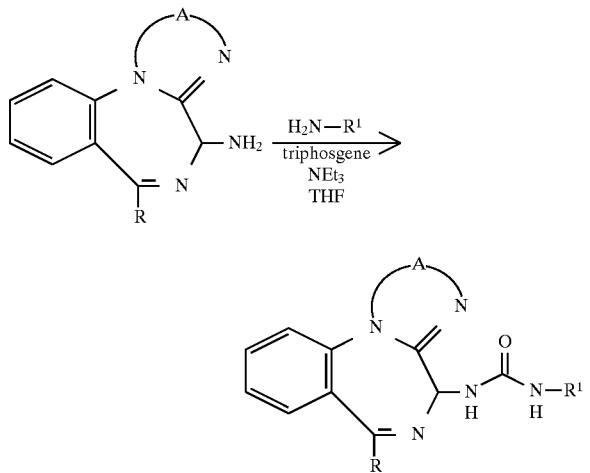

In this process, an amine $H_2N—R^1$ in THF at about −10° to +10° C. is treated with triethylamine and triphosgene at about pH 8.5. After 5–10 minutes at −10° to +10° C. and 5–10 minutes at ambient temperature, the mixture is treated with the aminobenzodiazepine at about −10° to +10° C. for about 5 to 20 minutes.

A fourth novel process of this invention is depicted as follows:

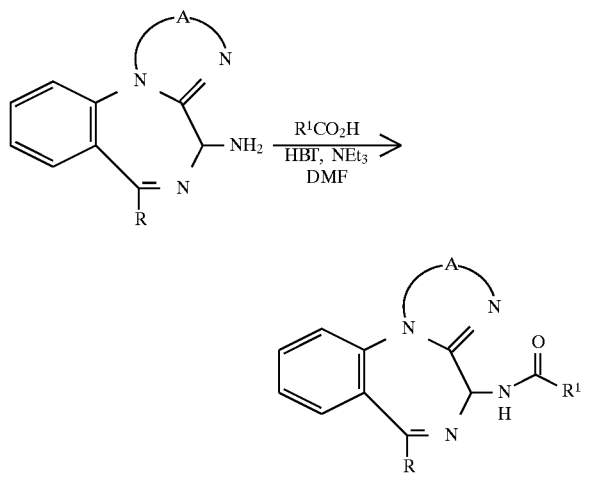

In this process the aminobenzodiazepine; the carboxylic acid, $R^1CO_2H$; 1-hydroxybenzotriazole hydrate (HBT); 1-ethyl-3-(3-dimethylaminopropyl)carbodiimide; and triethylamine in DMF is stirred at about room temperature until the reaction is complete, usually about 15 to 24 hours.

EXAMPLE 1

Preparation of N-[(2S,4R)-methyl-6-phenyl-2,4-dihydro-1H-imidazo [1,2-a][1,4]benzodiazepin-4-yl]-N'-[3-methylphenyl]-urea and N-[(2S,4S)-methyl-6-phenyl-2,4-dihydro-1H-imidazo[1,2-a][1,4]-benzodiazepin-4-yl]-N'-[3-methylphenyl]-urea Step A: Synthesis of N-{(S)-(+)-2-amino-[(R,S)-3-(((3-methylphenyl) amino)carbonyl)amino]-5-phenyl-2H-1,4-benzodiazepin-2-yl}-1-propanol (R,S)-N-(2,3-Dihydro-2-thiono-5-phenyl- 1H- 1,4-benzo-diazepin-3-yl)-N'-(3-methylphenyl)-urea (382 mg, 0.954 mmole) (U.S. Pat. No. 4,820,834) was dissolved in 10 ml of dry tetrahydrofuran and treated in succession with (S)-(+)-2-amino-1-propanol (297 μL, 3.82 mmole) and mercuric chloride 337 mg. The resulting suspension was then heated at 55° C. for 2 hr. The reaction mixture was filtered and the filter cake was washed with tetrahydrofuran. The filtrate was concentrated in vacuo and the residue was flash chromatographed on silica gel (2% methanol in chloroform) to yield 415 mg (95% yield) of the analytical product as a mixture of diastereomers: m.p. 137°–140° C.

$^1$HNMR (CDCl$_3$): Consistent with structure and confirms solvate form;

HPLC:>99% pure at 214 nM; $R_f$=0.27 (CHCl$_3$—CH$_3$OH; 92:8) FAB MS: 442(M$^+$+H);

Elem. Anal. calc'd for $C_{26}H_{27}N_5O_2.0.5CHCl_3.0.35CH_3OH$: Calc'd: C,62.93; H,5.68; N,13.67. Found: C,62.97; H,5.50; N,13.45.

Step B: Cyclization of N-{(S)-(+)-2-amino-[(R,S)-3-(((3-methylphenyl)-amino) carbonyl)amino]-5-phenyl-2H-1,4-benzodiazepin-2-yl}-1-propanol An ice cold solution of 430 mg (0.974 mmole) of N-{(S)-(+)-2-amino-[(R,S)-3-(((3-methylphenyl)-amino) carbonyl) amino]-5-phenyl-2H-1,4-benzodiazepin-2-yl}-1-propanol in 17 ml of methylene chloride was protected from moisture and treated with methanesulfonyl chloride (91 μL, 1.17 mmole) and diisopropylethylamine (356 μL, 2.04 mmole). After 15 minutes the reaction mixture was allowed to warm to room temperature and stirring was continued for 1.5 hours more. All volatiles were removed under reduced pressure and the residue was dissolved in 190 ml of ethyl acetate. The organic phase was washed once with 10% citric acid solution containing brine (50% by volume), with 10% sodium carbonate solution (2×20 ml), and then with brine. The organic extracts were then dried (sodium sulfate) and concentrated to yield 427 mg of crude product as a mixture of diastereomers. This material was purified to homogeneity via HPLC employing a Rexchrom Pirkle Covalent L-Leucine column (5μ, 100A). (Chromatography conditions: 1:1 hexane-isopropanol eluant containing 0.2% triethyl-amine; 2 ml/min flow rate) In this way, N-[(2S,4R)-methyl-6-phenyl-2,4-dihydro- 1H-imidazo [1,2-a][1,4] benzo-diazepin-4-yl]-N'-[3-methyl-phenyl]-urea, with retention time of 6.95 minutes was obained in 99.7% chemical purity and 95% diastereomeric purity: m.p. 149° C.(d).

$^1$HNMR (CDCl$_3$): Consistent with structure and confirms solvate form;

HPLC: >99% pure at 214 nM; $R_f$=0.19 (ethyl acetate-hexane; 7:3)

FAB MS: 424 (M$^+$+H);

Elem. Anal. calc'd for $C_{26}H_{25}N_5O.0.5CHCl_3.0.05CH_3OH$: Calc'd: C,71.86; H, 5.83; N, 16.03. Found: C,71.84; H,5.88; N,15.86.

N-[(2S,4S)-methyl-6-phenyl-2,4-dihydro-1H-imidazo [1,2-a][1,4]benzodiazepin-4-yl]-N'-[3-methylphenyl]-urea, with retention time of 11.47 minutes was obained in 99.5% chemical purity and 98.5% diastereomeric purity: m.p. 155° C.(d).

$^1$HNMR (CDCl$_3$): Consistent with structure and confirms solvate form;

HPLC: >99% pure at 214 nM; $R_f$=0.33 (ethyl acetate-hexane; 7:3)

FAB MS: 424(M$^+$+H);

Elem. Anal. calc'd for $C_{26}H_{25}N_5O.0.5CHCl_3.0.1Hexane$: Calc'd: C,66.18; H,5.51; N,14.24. Found: C,66.40; H,5.44; N,14.24.

EXAMPLE 2

Preparation of N-[(4R,4S)-6-phenyl-2,4-dihydro-1H-imidazo [1,2-a][1,4]benzodiazepin-4-yl]-N'-[3-methylphenyl]-urea (R,S)-N-(2,3-Dihydro-2-thiono-5-phenyl-1H-1,4-benzodiazepin-3-yl)-N'-(3-methylphenyl)-urea and ethanolamine were used to prepare N-{2-amino-[(R,S)-3-(((3-methylphenyl)-amino) carbonyl)-amino]-5-phenyl-2H-1,4-benzodiazepin-2-yl}-ethanol (m.p. 169°–170° C.) according to Example 1, Step A. The latter compound was then converted to the title compound employing reaction conditions identical to those described in Example 1, Step B. The analytical product was obtained as a white solid via flash chromatography on silica gel (chloroform-methanol, 88:12) followed by trituration of the chromatographed product with ethyl ether: m.p. 147° C.(d).

$^1$HNMR(CDCl$_3$): Consistent with structure and confirms solvate form;
HPLC: >91% pure at 214 nM; R$_f$=0.3(CHCl$_3$—CH$_3$OH;9:1)
FAB MS: 410(M$^+$+H);
Elem. Anal. calc'd for C$_{25}$H$_{23}$N$_5$O.0.15CHCl$_3$.0.75CH$_3$OH: Calc'd: C,68.90; H,5.84; N,15.52. Found: C,68.92; H,5.67; N,15.18.

EXAMPLE 3

Preparation of N-[(2R,4R,4S)-methyl-6-phenyl-2,4-dihydro-1H-imidazo [1,2-a][1,4]benzodiazepin-4-yl]-N'-[3-methylphenyl]-urea (R,S)-N-(2,3-Dihydro-2-thiono-5-phenyl-1H-1,4-benzodiazepin-3-yl)-N'-(3-methylphenyl)-urea and (R)-(-)-2-amino-1-propanol were used to prepare N-{(R)-(-)-2-amino-[(R,S)-3-(((3-methylphenyl) amino)carbonyl)-amino]-5-phenyl-2H-1,4-benzodiazepin-2-yl}-1-propanol according to Example 1, Step A. The latter compound was then converted in 76% yield to the title compound (as a mixture of diastereomers) employing reaction conditions identical to those described in Example 1, Step B: m.p. 141° C. (d).

$^1$HNMR (CDCl$_3$): Consistent with structure and confirms solvate form;
HPLC: Isomer A & B>95% pure at 214 nM; Isomer A: R$_f$=0.33 (ethyl acetat-hexane, 4:1), Isomer B: R$_f$=0.42 (ethyl acetat-hexane, 4:1)
FAB MS: 424(M$^+$+H);
Elem. Anal. calc'd for C$_{26}$H$_{25}$N$_5$O.0.65Ether.0.10Hexane: Calc'd: C,73.01; H,6.90; N,14.58. Found: C,72.99; H,6.62; N,14.20.

EXAMPLE 4

Preparation of N-[(1R,4R,4S)-methyl-6-phenyl-2,4-dihydro-1H-imidazo [1.2-a][1,4]benzodiazepin-4-yl]-N'-[3-methylphenyl]-urea (R,S)-N-(2,3-Dihydro-2-thiono-5-phenyl-1H-1,4-benzodiazepin-3-yl)-N'-(3-methylphenyl)-urea (180 mg, 0.449 mmole) and (R)-(-)-1-amino-2-propanol (142 μL, 1.796 mmole) were used to prepare 70 mg of N-{(R)-(-)-1-amino-[(R,S)-3-(((3-methylphenyl)-amino) carbonyl)-amino]-5-phenyl-2H-1,4-benzodiazepin-2-yl}-2-propanol according to Example 1, Step A. The latter compound was then converted in 96% yield to the title compound (as a mixture of diastereomers) employing reaction conditions identical to those described in Example 1, Step B: m.p. 140° C.(d).

$^1$HNMR (CDCl$_3$): Consistent with structure and confirms solvate form;
HPLC: 97.6% pure at 214 nM; R$_f$=0.16 (ethyl acetat-hexane, 7:3);
FAB MS: 424(M$^+$+H);
Elem. Anal. calc'd for C$_{26}$H$_{25}$N$_5$O.0.05CHCl$_3$.0.10Hexane: Calc'd: C,73.06; H,6.09; N,15.99. Found: C,72.88; H,6.00; N,15.71.

EXAMPLE 5

Preparation of N-[(5R,5S)-7-phenyl-1,2,3,5-tetrahydro- pyrimido [1,2-a][1,4]benzodiazepin-5-yl]-N'-[3-methylphenyl]-urea (R,S)-N-(2,3-Dihydro-2-thiono-5-phenyl-1H-1,4-benzodiazepin-3-yl)-N'-(3-methylphenyl)-urea (135 mg, 0.337 mmole) and 1-propanolarnine (102 μL, 1.35 mmole) were used to prepare 110 mg (74% yield) of N-{3-amino-[(R,S)-3-(((3-methylphenyl)-amino) carbonyl)amino]-5-phenyl-2H-1,4-benzodiazepin-2-yl}-propanol (m.p. 195°–196° C.) according to Example 1, Step A. The latter compound was then converted to the title compound employing reaction conditions identical to those described in Example 1, Step B. The analytical product was obtained as a white solid in 82% yield via flash chromatography on silica gel (chloroform-methanol, 88:12) followed by trituration of the chromatographed product with an ethyl ether-petroleum ether solvent mix: m.p. 172°–174° C.(d).

$^1$HNMR (CDCl$_3$): Consistent with structure and confirms solvate form;
HPLC: >99% pure at 214 nM; R$_f$=0.2(CHCl$_3$—CH$_3$OH; 9:1)
FAB MS: 424(M$^+$+H);
Elem. Anal. calc'd for C$_{26}$H$_{25}$N$_5$O.0.5CHCl$_3$.1.35CH$_3$OH: Calc'd: C,63.53; H,5.92; N,13.30. Found: C,63.51; H,5.94; N,13.55.

EXAMPLE 6

Preparation of N-[(2S,4R)-methyl-5-cyclohexyl-2,4-dihydro-1H-imidazo [1,2-a][1,4]benzodiazepin-4-yl]-N'-[3-methylphenyl]-urea and N-[(2S,4S)-methyl-5-cyclohexyl-2,4-dihydro- 1H-imidazo[1,2-a][1,4]benzodiazepin-4-yl]-N'-[3-methylphenyl]-urea Step A: Synthesis of 1,3-dihydro-5-cyclohexyl-3(R,S)-[(benzyloxy-carbonyl) amino]-2H-1.4-benzodiazepin-2-thione 1,3-Dihydro-5-cyclohexyl-3(R,S)-[(benzyloxycarbonyl)-amino]-2H-1,4-benzodiazepin-2-one (M. Chambers, et. al. *Biomed. Chem. Lett.* 1993, in press) (1.09 g, 2.79 mmole) was mixed with 1.13 g (2.79 mmole) of 2,4-bis(4-methoxyphenyl)-1,3-dithia-2,4-diphosphetane-2,4-disulfide in 26 ml of toluene. The resulting suspension was heated to reflux for 1 hour. The reaction mixture was cooled, filtered, and concentrated in vacuo. The residue was flash chromatographed on silica gel (ethyl acetate-hexane, 1:3) and the product containing fractions were pooled and concentrated to give the title compound in approximately 85% purity. This material was recrystallized from hexane-ethyl acetate (1:1) to give 850 mg (75%) of the title compound in analytical form: m.p. 164°–165° C.

Step B: Synthesis of 1,3-dihydro-5-cyclohexyl-3(R,S)-amino-2H-1.4-benzodiazepin-2-thione 1,3-Dihydro-5-cyclohexyl-3(R,S)-[(benzyloxycarbonyl)-amino]-2H-1,4-benzodiazepin-2-thione (787 mg, 1.93 mmole) was dissolved in 40 ml of a 1:1 mixture of methylene chloride and acetic acid. The resulting solution was cooled to 0° C. and a continuous stream of hydrogen bromide gas was passed into the stirred solution for 10 minutes. The reaction vessel was capped and the reaction mixture was allowed to warm to ambient temperature over 5 hours. All volatiles were removed under reduced pressure and the yellow residual solid was azeotropically dried with toluene. This material was partitioned between 180 ml of ethyl acetate and 7.3 ml of 10% sodium carbonate solution. The resulting suspension was stirred for 5 minutes and then filtered. The filter cake was washed with ethyl acetate, dried in vacuo over phosporus pentoxide (40° C.), and triturated with ethyl acetate-hexane (1:1) to give 492 mg of the title compound (93% yield).

Step C: Synthesis of (R,S)-N-[2,3-dihydro-2-thiono-5-cyclohexyl-2H-1,4-benzodiazepin-3-yl]-N'-[3-methylphenyl1]-urea 1,3-Dihydro-5-cyclohexyl-3(R,S)-amino-2H-1,4-benzodiazepin-2-thione (240 mg, 0.878 mmole) and 124 $\mu$L of m-tolylisocyanate were combined in 22 ml of tetrahydrofuran at 0° C. under nitrogen. The reaction mixture was allowed to warm to ambient temperature over a 45 minute period and was filtered. The filtrate was concentrated under reduced pressure and the residue was chromato-graphed on silica gel eluting initially with chloroform and then with 1% methanol in chloroform. The title compound was thus obtained in 92% yield as a racemic mixture whose $^1$HNMR spectrum confirmed the structure assignment.

Step D: Synthesis of N-{(S)-(+)-2-amino-[(R,S)-3-(((3-methylphenyl) amino)carbonyl)amino]-5-cyclohexyl-2H-1,4-benzodiazepin-2-yl}-1-propanol Employing conditions identical to those described in Example 1, Step A, (R,S)-N-[2,3-dihydro-2-thiono-5-cyclohexyl-2H-1,4-benzodiazepin-3-yl]-N'-[3-methylphenyl]-urea (330 mg, 0.812 mmole) was reacted with (S)(-(+)-2-amino-1-propanol and 287 mg of mercuric chloride in 8 ml of tetrahydrofuran to yield 363 mg of the title compound as a mixture of diastereomers. ($^1$HNMR (CDCl$_3$): Confirms structure assignment.)

Step E: Cyclization of N-{(S)-(+)-2-amino-[(R,S)-3-(((3-methylphenyl)-amino) carbonyl)amino]-5-cyclohexyl-2H-1,4-benzodiazepin-2-yl}1-propanol N-{(S)-(+)-2-Amino-[(R,S)-3-(((3-meffiylphenyl)-amino)-carbonyl) amino]-5-cyclohexyl-2H-1,4-benzodiazepin-2-yl}-1-propanol (365 mg) was converted to the title compounds according to the procedure outlined in Example 1, Step B. Separation of the final product diastereomeric mixture via chiral preparative HPLC chromatography (cf. Example 1, Step B) yielded N-[(2S,4R)-methyl-6-cyclohex-yl-2,4-dihydro-1H-imidazo [1,2-a][1,4]benzodiazepin4-yl]-N'-[3-methyl-phenyl]-urea with 97% diastereomeric purity: m.p. 166° C.
$^1$HNMR (CDCl$_3$): Consistent with structure and confirms solvate form;
HPLC: >97% pure at 214 nM; R$_f$=0.16 (ethyl acetate-hexane; 7:3)
FAB MS: 430(M$^+$+H).

N-[(2S,4S)-methyl-6-cyclohexyl-2,4-dihydro-1H-imidazo-[1,2-a][1,4]-benzodiazepin-4-yl]-N'-[3-methylphenyl]-urea was obained in 99.5% chemical purity and 70% diastereomeric purity: m.p. 142° C.(d).
$^1$HNMR(CDCl$_3$): Consistent with structure and confirms solvate form;
HPLC: >99% pure at 214 nM; R$_f$=0.30 (ethyl acetate-hexane; 7:3)
FAB MS: 430(M$^+$+H);

Elem. Anal. calc'd for C$_{26}$H$_{31}$N$_5$O.0.4CHCl$_3$.0.15Ethyl acetate: Calc'd: C,66.11; H,6.70; N,14.28. Found: C,66.38; H,6.46; N,14.24.

EXAMPLE 7

Preparation of N-[(2S,4R,4S)-methyl-6-phenyl-2,4-dihydro-1H-imidazo [1,2-a][1,4]benzodiazepin-4-yl]-N'-[4-Chlorophenyl]-urea (R,S)-N-(2,3-Dihydro-2-thiono-5-phenyl-1H-1,4-benzodiazepin-3-yl)-N'-(4-chlorophenyl)-urea and (R)-(–)-2-amino-1-propanol were used to prepare N-{(R)-(–)-2-amino-[(R,S)-3-(((4-chlorophenyl) amino)carbonyl)-aniino]-5-phenyl-2H-1,4-benzodiazepin-2-yl}-1-propanol according to Example 1, Step A. The latter compound was then converted to the title compound (as a mixture of diastereomers) employing reaction conditions identical to those described in Example 1, Step B: m.p. 164° C.(d).
$^1$HNMR (CDCl$_3$): Consistent with structure and confirms solvate form;
HPLC: Isomer A & B>95% pure at 214 nM; R$_f$=0.67 (chloroform-methanol, 9:1);
FAB MS: 444(M$^+$+H);
Elem. Anal. calc'd for C$_{25}$H$_{22}$ClN$_5$O: Calc'd: C,67.64; H,5.00; N,15.78. Found: C,67.24; H,5.13; N,13.14.

EXAMPLE 8

Preparation of N-[(2S,4R,4S)-methyl-6-phenyl-2,4-dihydro-1H-imidazo [1,2-a][1,4]benzodiazepin-4-yl]-N'-[3-Chlorophenyl]-urea (R,S)-N-(2,3-Dihydro-2-thiono-5-phenyl-1H-1,4-benzodiazepin-3-yl)-N'-(3-chlorophenyl)-urea and (R)-(–)-2-amino-1-propanol were used to prepare N-{(R)-(–)-2-amino-[(R,S)-3-(((4-chlorophenyl) amino)carbonyl)-amino]-5-phenyl-2H-1,4-benzodiazepin-2-yl}-1-propanol according to Example 1, Step A. The latter compound was then converted to the title compound (as a mixture of diastereomers) employing reaction conditions identical to those described in Example 1, Step B: m.p. 143°–146° C.(d).
$^1$HNMR (CDCl$_3$): Consistent with structure and confirms solvate form;
HPLC: Isomer A & B>95% pure at 214 nM; R$_f$=0.68 (chloroform-methanol, 9:1);
FAB MS: 444(M$^+$+H);
Elem. Anal. calc'd for C$_{25}$H$_{22}$ClN$_5$O.0.45EtOAc.0.2CHCl$_3$: Calc'd: C,63.91; H,5.12; N,13.80. Found: C,63.69; H,5.22; N,13.91.

EXAMPLE 9

Preparation of N-[(2S,4R,4S)-methyl-6-phenyl-2,4-dihydro-1H-imidazo [1,2-a][1,4]benzodiazepin-4-yl]-N'-[4-Trifluoromethylphenyl]-urea (R,S)-N-(2,3-Dihydro-2-thiono-5-phenyl-1H-1,4-benzodiazepin-3-yl)-N'-(4-trifluoromethylphenyl)-urea and (R)-(–)-2-amino-1-propanol were used to prepare N-{(R)-(–)-2-amino-[(R,S)-3-(((4-chlorophenyl) amino)carbonyl)-amino]-5-phenyl-2H-1,4-benzodiazepin-2-yl}-1-propanol according to Example 1, Step A. The latter compound was then converted to the title compound (as a mixture of diastereomers) employing reaction conditions identical to those described in Example 1, Step B: m.p. 148°–152° C.(d).
$^1$HNMR (CDCl$_3$): Consistent with structure and confirms solvate form;
HPLC: Isomer A & B>96% pure at 214 nM; R$_f$=0.66 (chloroform-methanol, 9:1);

FAB MS: 478 (M$^+$+H);

Elem. Anal. calc'd for C$_{26}$H$_{22}$FN$_5$O.0.45 2-propanol: Calc'd: C,65.10; H,5.11; N,13.88. Found: C,65.23; H,4.88; N,13.85.

EXAMPLE 10

Preparation of N-[(2S,4S)-methyl-5-cyclohexyl-2,4-dihydro-1H-imidazo [1,2-a][1,4]benzodiazepin-4-yl]-N'-[6-indolyl]-urea and N-[(2S,4R)-methyl-5-cyclohexyl-2,4-dihydro-1H-imidazo[1,2-a][1,4]benzodiazepin-4-yl]-N'- [6-indolyl]-urea Step A: Synthesis of N-{(S)-(+)-2-amino-[(R,S)-3-(benzyloxy-carbonyl) amino]-5-cyclohexyl-2H-1,4-benzodiazepin-2-yl}-1-propanol 1,3-Dihydro-5-cyclohexyl-3(R,S)-[(benzyloxycarbonyl)-amino]-2H-1,4-benzodiazepin-2-thione (1 g, 2.45 mmole) was dissolved in 8 ml of dry tetrahydrofuran and treated in succession with (S)-(+)-2-amino-1-propanol (763 μL, 9.80 mmole) and mercuric chloride 866 mg. The resulting suspension was then heated at 55° C. for 2 hr. The reaction mixture was filtered and the filter cake was washed with tetrahydrofuran. The filtrate was concentrated in vacuo and the residue was flash chromatographed on silica gel (ethyl acetate-hexane gradient, 20–60% ethyl acetate) to yield 1.17 g (61% yield) of the analytical product as a mixture of diastereomers: R$_f$=0.3 (ethyl acetate-hexane, 1:1);
$^1$HNMR (CDCl$_3$): Consistent with structure.

Step B: Cyclization of N-{(S)-(+)-2-amino-[(R,S)-3-(benzyloxy-carbonyl) amino]-5-cyclohexyl-2H-1,4-benzodiazepin-2-yl}-1-propanol An ice cold solution of 670 mg (1.49 mmole) of N-{(S)-(+)-2-amino-[(R,S)-3-(benzyloxycarbonyl) amino]-5-cyclohexyl-2H-1,4-benzodiazepin-2-yl}-1-propanol in 26 ml of methylene chloride was protected from moisture and treated with methanesulfonyl chloride (139 μL, 1.79 mmole) and diisopropylethylamine (544 μL, 3.13 mmole). After 15 minutes the reaction mixture was allowed to warm to room temperature and stirring was continued for 1.5 hours more. All volatiles were removed under reduced pressure, the residue was azeotroped with toluene and then dissolved in 200 ml of ethyl acetate. The organic phase was washed once with 10% citric acid solution containing brine (50% by volume), with 10% sodium carbonate solution (2×20 ml), and then with brine. The organic extracts were then dried (sodium sulfate) and concentrated to yield 567 mg of crude product as a mixture of diastereomers. This material was taken directly to the next Step C.

Step C: Preparation of (4R,4S)-amino-(2S)-methyl-6-cyclohexyl-2,4-dihydro-1H-imidazor [1,2-a][1,4]benzodiazepine (4R,4S)-(Benzyloxycarbonyl)amino-(2S)-methyl-6-cyclohexyl-2,4-dihydro-1H-imidazo [1,2-a][1,4]benzodiazepine (250 mg, 0.581 mmole) was dissolved in 8 ml of dry methanol and treated with 150 mg of 10% palladium/carbon catalyst. The resulting suspension was stirred at ambient temperature for 1.25 hours under a hydrogen atmosphere. The reaction mixture was filtered and the catalyst was washed with methanol. The filtrated was concentrated in vacuo and the residue was azeotropically dried with toluene to give 159 mg of the product.

Step D: Reaction of (4R,4S)-amino-(2S)-methyl-6-cyclohexyl-2,4-dihydro-1H-imidazo [1,2-a][1,4]benzodiazepine with 6-indolylisocyanate 6-Aminoindole (92.1 mg, 0.232 mmole) was dissolved in 17 ml of tetrahydrofuran at 0° C. and treated with 97 μL of triethyl-amine. To this mixture was added 69 mg (0.232 mmole) of triphosgene. More triethylamine was added until the pH of the reaction mixture registered 8.5 using moist pH paper. The reaction mixture was stirred at 0° C. for 5 minutes and at ambient temperature for 5 minutes more. The reaction mixture was recooled to 0° C. and treated with 159 mg (0.536 mmole) of (4R,4S)-amino-(2S)-methyl-6-cyclohexyl-2,4-dihydro-1H-imidazo [1,2-a][1,4] benzodiazepine in 10 ml of tetrahydro-furan. After 10 minutes the reaction mixture was filtered and the filtrate was concentrated. The resulting residue was partitioned between 10% citric acid solution and ethyl acetate (75 ml). The organic phase was then washed in succession with 10% sodium carbonate solution and brine, then dried and concentrated to give 323 mg of the crude product. Separation of the final product diastereomeric mixture via chiral preparative HPLC chromatography (cf. Example 1, Step B) yielded 83 mg of N-[(2S,4S)-methyl-5-cyclohexyl-2,4-dihydro-1H-imidazo [1,2-a][1,4]benzodiazepin-4-yl]-N'-[6-indolyl]-urea with 99% diastereomeric purity: m.p. 180° C.
$^1$HNMR (CDCl$_3$): Consistent with structure and confirms solvate form;
HPLC: >97% pure at 214 nM; R$_f$=0.52 (hexane-2-propanol; 3:1)
FAB MS: 455(M$^+$+H).

Elem. Anal. calc'd for C$_{27}$H$_{30}$N$_6$O.0.35CHCl$_3$.0.75CH$_3$OH: Calc'd: C,64.85; H,6.46; N,16.15. Found: C,64.84; H,6.09; N,15.81.

N-[(2S ,4R)-methyl-5-cyclohexyl-2,4-dihydro-1H-imidazo [1,2-a][1,4]benzodiazepin-4-yl]-N'-[6-indolyl]-urea (153 mg total) was obained in >99% diastereomeric purity and >98% chemical homogeneity: m.p. 191° C.(d).
$^1$HNMR (CDCl$_3$): Consistent with structure and confirms solvate form;
HPLC: >98% pure at 214 nM; R$_f$=0.38(hexane-2-propanol; 3:1)
FAB MS: 455 (M$^+$+H).

Elem. Anal. calc'd for C$_{27}$H$_{30}$N$_6$O.0.35CHCl$_3$.0.75CH$_3$OH: Calc'd: C,64.85; H,6.46; N,16.15. Found: C,64.83; H,6.15; N,15.79.

EXAMPLE 11

Preparation of N-[(2S,4S)-methyloxycarbonyl-6-phenyl-2,4-dihydro-1H-imidazo [1,2-a][1,4]benzodiazepin-4-yl]-N'-[3-methylphenyl]-urea and N-[(2S,4R)-methyloxycarbonyl-6-phenyl-2,4-dihydro-1H-imidazor [1,2-a][1,4]benzodiazepin-4-yl]-N'-[3-methylphenyl]-urea (R,S)-N-(2,3-Dihydro-2-thiono-5-phenyl-1H-1,4-benzodiazepin-3-yl)-N'-(3-methylphenyl)-urea (120 mg, 0.3 mmole) and (D)-serine methyl ester hydrochloride 187 mg (1.2 mmole) were used to prepare 140 mg of methyl N-(R)-2-amino-{[(R,S)-3-(((3-methylphenyl) amino) carbonyl)amino]-5-phenyl-2H-1,4-benzodiazepin-2-yl}-2-hydroxypropanoate according to the procedure of Example 1, Step A. The latter compound was then converted to the title compound (as a mixture of diastereomers) employing reaction conditions identical to those described in Example 1, Step B. Separation of the final product diastereomeric mixture was accomplished by flash chromatography on silica gel (70% ethyl acetate initially and then 80% ethyl acetate-hexane) yielding 50 mg of N-[(2S,4S)-methyloxycarbonyl-6-phenyl-2,4-dihydro-1H-imidazo[1,2-a][1,4]benzodiazepin-4-yl]-N'-[3-methyl-phenyl]-urea after trituration with ether-hexane solution: m.p. 152° C. (d).

¹HNMR (CDCl₃): Consistent with structure and confirms solvate form;
HPLC: >88% diastereomeric purity and >93% chemical at 214 nM;
$R_f$=0.62 (ethyl acetate-hexane; 4:1)
FAB MS: 468(M⁺+H).
Elem. Anal. calc'd for $C_{27}H_{25}N_5O_3 \cdot 0.25CHCl_3 \cdot 0.10OEtOAc$: Calc'd: C,65.60; H,5.19; N,13.84. Found: C,65.73; H,5.25; N,13.77.
N-[(2S,4R)-methyloxycarbonyl-6-phenyl-2,4-dihydro-1H-imidazo [1,2-a][1,4]benzodiazepin-4-yl]-N'-[3-methylphenyl]-urea (20 mg) was obained in >77% diastereomeric purity and >95% chemical homogeneity: m.p. 137°–140° C.(d).
¹HNMR (CDCl₃): Consistent with structure and confirms solvate form;
HPLC: >95% pure at 214 nM; $R_f$=0.35 (ethyl acetate-hexane; 4:1)
FAB MS: 468(M⁺+H).
Elem. Anal. calc'd for $C_{27}H_{25}N_5O_3 \cdot 0.4CHCl_3$: Calc'd: C,63.86; H,4.97; N,13.59. Found: C,63.74; H,5.13; N,13.32.

EXAMPLE 12

Preparation of N-[6-phenyl-2,4-dihydro-4H-imidazo [1,2-a][1,4]benzo-diazepin-4-yl]-N'-[3-methylphenyl]-urea (R,S)-N-(2,3-Dihydro-2-thiono-5-phenyl-1H-1,4-benzodiazepin-3-yl)-N'-(3-methylphenyl)-urea (153 mg, 0.382 mmole) and aminoacetaldehyde dimethylacetal 167 μL (1.528 mmole) were used to prepare 196 mg of N-2-amino-{[(R,S)-3-(((3-methylphenyl)amino)-carbonyl) amino]-5-phenyl-2H-1,4-benzodiazepin-2-yl}-1-acetaldehyde dimethylacetal according to the procedure of Example 1, Step A. The latter compound (180 mg) was dissolved in 5 ml of methylene chloride and treated with 1.5 ml of borontrifluoride etherate. The reaction mixture was stirred at 50° C. for 2.5 hours, cooled, diluted with 250 ml of ethyl acetate. The resulting solution was washed with 10% sodium carbonate solution and brine, then dried and concentrated to give 180 mg of the title compound in crude form. The analytical material was obtained after preparative thick layer chromatography on silica gel (chloroform-methanol elution, 96:4): m.p. 144° C.(d).
¹HNMR (CDCl₃): Consistent with structure and confirms solvate form;
HPLC: >99% pure at 214 nM; $R_f$=0.53 (chloroform-methanol; 9:1)
FAB MS: 408(M⁺+H).
Elem. Anal. calc'd for $C_{25}H_{21}N_5O \cdot 0.4CHCl_3$: Calc'd: C,67.01; H,4.74; N,15.39. Found: C,66.94; H,4.87; N,15.35.

EXAMPLE 13

Preparation of N-[(1R,4S)-methyl-6-phenyl-2,4-dihydro-1H-imidazo [1,2-a][1,4]benzodiazepin-4-yl]-N'-[3-methylphenyl]-urea and N-[(1R,4R)-methyl-6-phenyl-2,4-dihydro-1H-imidazo[1,2-a][1,4]benzodiazepin-4-yl]-N'-[3-methylphenyl]-urea Step A: Synthesis of N-{(2S)-(+)-3-amino-[(R,S)-3-(((3-methyl-phenyl)amino)carbonyl)amino]-5-phenyl-2H-1,4-benzo-diazepin-2-yl}-2-propanol (R,S)-N-(2,3-Dihydro-2-thiono-5-phenyl-1H-1,4-benzodiazepin-3-yl)-N'-(3-methylphenyl)-urea (460 mg, 1.15 mmole) was dissolved in 20 ml of dry tetrahydrofuran and treated in succession with (S)-(+)-1-amino-2-propanol (363 μL, 4.6 mmole) and mercuric chloride 406 mg. The resulting suspension was then heated at 55° C. for 2 hr. The reaction mixture was filtered and the filter cake was washed with tetrahydrofuran. The filtrate was concentrated in vacuo and the residue was flash chromatographed on silica gel (2% methanol in chloroform) to yield 390 mg (77% yield) of the analytical product as a mixture of diastereomers;
¹HNMR (CDCl₃): Consistent with structure.
Step B: Cyclization of N-{(S)-(+)-3-amino-[(R,S)-3-(((3-methyl-phenyl)-amino) carbonyl)amino]-5-phenyl-2H-1,4-benzo-diazepin-2-yl}-2-propanol An ice cold solution of 390 mg (0.883 mmole) of N-{(S)-(+)-3-amino-[(R,S)-3-(((3-methylphenyl)-amino)carbonyl) amino]-5-phenyl-2H-1,4-benzodiazepin-2-yl}-2-propanol in 20 ml of methylene chloride was protected from moisture and treated with methanesulfonyl chloride (82 μL, 1.06 mmole) and diisopropylethylamine (323 μL, 1.86 mmole). After 15 minutes the reaction mixture was allowed to warm to room temperature and stirring was continued for 24 hours more. All volatiles were removed under reduced pressure and the residue was dissolved in 190 ml of ethyl acetate. The organic phase was washed once with 10% citric acid solution containing brine (50% by volume), with 10% sodium carbonate solution (2×20 ml), and then with brine. The organic extracts were then dried (sodium sulfate) and concentrated to yield 370 mg of crude product as a mixture of diastereomers. This material was purified to homogeneity via HPLC employing a Rexchrom Pirkle Covalent L-Leucine column (5μ, 100A). (Chromatography conditions: 1:1 hexane-isopropanol eluant containing 0.2% triethylamine; 2 ml/min flow rate). In this way, N-[(1R,4S)-methyl-6-phenyl-2,4-dihydro-1H-imidazo[1,2-a][1,4] benzodiazepin-4-yl]-N'-[3-methylphenyl]-urea was obained in excess of 99% diastereomeric purity: m.p. 135°–138° C.(d).
¹HNMR (CDCl₃): Consistent with structure and confirms solvate form;
HPLC: >99% pure at 214 nM; $R_f$=0.14 (ethyl acetate-hexane; 4:1)
FAB MS: 424(M⁺+H);
Elem. Anal. calc'd for $C_{26}H_{25}N_5O \cdot 0.25CHCl_3 \cdot 0.15hexane$: Calc'd: C, 69.93; H,5.91; N,15.02. Found: C,69.95; H,5.73; N,15.04.
N-[(1R,4R)-methyl-6-phenyl-2,4-dihydro-1H-imidazo[1,2-a][1,4]benzodiazepin-4-yl]-N'-[3-methylphenyl]-urea was obtained in 99% diastereomeric purity: m.p. 145°–148° C.(d).
¹HNMR (CDCl₃): Consistent with structure and confirms solvate form;
HPLC: >99% pure at 214 nM; $R_f$=0.14 (ethyl acetate-hexane; 4:1)
FAB MS: 424(M⁺+H);
Elem. Anal. calc'd for $C_{26}H_{25}N_5O \cdot 0.35CHCl_3 \cdot 0.10i$-propanol: Calc'd: C,67.91; H,5.59; N,14.86. Found: C,68.15; H,5.58; N,14.59.

EXAMPLE 14

Preparation of (4S)-N-[(2S)-methyl-6-cyclohexyl-2, 4-dihydro-1H-imidazo [1,2-a][1,4]benzodiazepin-4-yl]-naphthalene-1-acetamide and (4R)-N-[(2S)-methyl-6-cyclohexyl-2,4-dihydro-1H-imidazo[1,2-a][1,4]benzodiazepin-4-yl]-naphthalene-1-acetamide 1-Naphthylacetic acid (45 mg, 0.242 mmole) was added to a solution of 3 ml of dry N,N-dimethylformamide containing 33 mg of 1-hydroxybenzotriazole hydrate (0.242 mmole). To this mixture was added 1-ethyl-3-(3-dimethylamininopropyl)carbodiimide hydrochloride (46 mg, 0.242 mmole) and (4R,4S)-amino-(2S)-methyl-6-cyclohexyl-2,4-dihydro-1H-imidazo [1,2-a][1,4] benzodiazepine (60 mg, 0.202 mmole), the latter prepared according to Example 10, Step C. The pH of the resulting reaction mixture was adjusted to 8.5 with triethylamine and this mixture was stirred at ambient temperature for 10 minutes under an inert atmosphere. The reaction mixture was concentrated under reduced pressure and the residue was partitioned between ethyl acetate and water. The organic phase was separated, washed with brine and dried. Concentration of the combined organic extracts yielded 173 mg of crude product. Purification to homogeneity of the product mixture was accomplished via HPLC employing a Rexchrom Pirkle Covalent L-Leucine column (5μ, 100A). (Chromatography conditions: 1:1 hexane-isopropanol eluant containing 0.2% triethylamine; 2 ml/min flow rate) In this way, (4S)-N-[(2S)-methyl-6-cyclohexyl-2,4-dihydro-1H-imidazo [1,2-a][1,4]benzodiazepin-4-yl]-naphthalene-1-acetamide was obained in excess of 75% diastereomeric purity: m.p. 127° C.(d).
$^1$HNMR (CDCl$_3$): Consistent with structure and confirms solvate form;
HPLC: >98% chemically pure at 214 nM; R$_f$=0.13 (ethyl acetate-hexane; 4:1)
FAB MS: 465(M$^+$+H);
Elem. Anal. calc'd for C$_{30}$H$_{32}$N$_4$O.0.4CHCl$_3$.0.15hexane: Calc'd: C,71.56 H,6.62; N,10.67. Found: C,71.66; H,6.61; N,10.98.
(4R)-N-[(2S)-methyl-6-cyclohexyl-2,4-dihydro-1H-imidazo[1,2-a][1,4]benzodiazepin-4-yl]-naphthalene-1-acetamide was obtained in 95% diastereomeric purity: m.p. 104° C.(d).
$^1$HNMR (CDCl$_3$): Consistent with structure and confirms solvate form;
HPLC: >99% pure at 214 nM; R$_f$=0.24 (ethyl acetate-hexane; 4:1)
FAB MS: 465(M$^+$+H);
Elem. Anal. calc'd for C$_{30}$H$_{32}$N$_4$O.0.1CHCl$_3$.0.25hexane: Calc'd: C,76.19; H,7.20; N,11.25. Found: C,76.50; H,6.95; N,11.23.

EXAMPLE 15

Preparation of N-[(2S,4S)-methyl-5-phenyl-2,4-dihydro-1H-imidazo [1,2-a][1,4]benzodiazepin-4-yl]-N'-[6-indolyl]-urea and N-[(2S,4R)-methyl-5-phenyl-2,4-dihydro-1H-imidazo[1,2-a][1,4]benzodiazepin-4-yl]-N'-[6-indolyl]-urea Step A: Synthesis of N-{(S)-(+)-2-amino-[(R,S)-3-(benzyloxy-carbonyl) amino]-5-phenyl-2H-1,4-benzodiazepin-2-yl}-1-propanol
1,3-Dihydro-5-phenyl-3(R,S)-[(benzyloxycarbonyl)amino]-2H-1,4-benzodiazepin-2-thione (3.5 g, 8.7 mmole) was dissolved in 100 ml of dry tetrahydrofuran and treated in succession with (S)-(+)-2-amino-1-propanol (1.36 ml, 17.40 mmole) and mercuric chloride (3.08 g, 11.3 mmole). The resulting suspension was then heated at 55° C. for 3 hr. The reaction mixture was filtered and the filter cake was washed with tetrahydrofuran. The filtrate was concentrated in vacuo and the residue was flash chromatographed on silica gel (ethyl acetate-hexane 1:1) to yield 1.16 g of the analytical product as a mixture of diastereomers:
$^1$HNMR (CDCl$_3$): Consistent with structure.

Step B: Cyclization of N-{(S)-(+)-2-amino-[(R,S)-3-(benzyloxy-carbonyl) amino]-5-phenyl-2H-1,4-benzodiazepin-2-yl}-1-propanol
An ice cold solution of 865 mg (1.96 mmole) of N-{(S)-(+)-2-amino-[(R,S)-3-(benzyloxycarbonyl)amino]-5-phenyl-2H-1,4-benzodiazepin-2-yl}-1-propanol in 35 ml of methylene chloride was protected from moisture and treated with methanesulfonyl chloride (182 μL, 2.35 mmole) and diisopropylethylamine (683 μL, 3.92 mmole). After 15 minutes the reaction mixture was allowed to warm to room temperature and stirring was continued for 1.5 hours more. All volatiles were removed under reduced pressure, the residue was azeotroped with toluene and then dissolved in 200 ml of ethyl acetate. The organic phase was washed once with 10% citric acid solution containing brine (50% by volume), with 10% sodium carbonate solution (2×20 ml), and then with brine. The organic extracts were then dried (sodium sulfate) and concentrated to yield 677 mg of crude product as a mixture of diastereomers. This material was taken directly to the next Step C.

Step C: Preparation of (4R,4S)-amino-(2S)-methyl-6-phenyl-2,4-dihydro-1H-imidazo[1,2][1,4]benzodiazepine
(4R,4S)-(Benzyloxycarbonyl)amino-(2S)-methyl-6-phenyl-2,4-dihydro-1H-imidazo [1,2-a][1,4]benzodiazepine (120 mg, 0.28 mmole) was dissolved in 25 ml of dry methanol and treated with 55 mg of 10% palladium/carbon catalyst. The resulting suspension was stirred at ambient temperature for 1.25 hours under a hydrogen atmosphere. An additional 50 mg of palladium catalyst was added and stirring was continued for 2 hours more. The reaction mixture was filtered and the catalyst was washed with methanol. The filtrated was concentrated in vacuo and the residue was azeotropically dried with toluene to give 86 mg of the product.

Step D: Reaction of (4R,4S)-amino-(2S)-methyl-6-phenyl-2,4-dihydro-1H-imidazo [1,2-a][1,4]benzodiazepine with 6-aminoindole
6-Aminoindole (71 mg) was dissolved in 14 ml of tetrahydrofuran at 0° C. and treated with 151 μL of triethylamine. To this mixture was added 53 mg (0.18 mmole) of triphosgene. More triethylamine was added until the pH of the reaction mixture registered 8.5 using moist pH paper. The reaction mixture was stirred at 0° C. for 5 minutes and at ambient temperature for 5 minutes more. The reaction mixture was recooled to 0° C. and treated with 133 mg (0.46 mmole) of (4R,4S)-amino-(2S)-methyl-6-phenyl-2,4-dihydro-1H-imidazo[1,2-a][1,4]benzodiazepine in 2 ml of tetrahydrofuran. After 10 minutes the reaction mixture was filtered and the filtrate was concentrated. The resulting residue was partitioned between 10% citric acid solution and ethyl acetate (75 ml). The organic phase was then washed in succession with 10% sodium carbonate solution and brine, then dried and concentrated. Separation of the final product diastereomeric mixture via chiral preparative HPLC chromatography (cf. Example 1, Step B) yielded 18 mg of N-[(2S,4S)-methyl-5-phenyl-2,4-dihydro-1H-imidazo [1,2-a][1,4]benzodiazepin-4-yl]-N'-[6-indolyl]-urea with 99% diastereomeric purity: m.p. 176°–180° C.
$^1$HNMR (CDCl$_3$): Consistent with structure and confirms solvate form;
HPLC: >99% pure at 214 nM;
FAB MS: 449(M$^+$+H).
Elem. Anal. calc'd for C$_{27}$H$_{24}$N$_6$O.0.35EtOAc.0.45H$_2$O: Calc'd: C,69.98; H,5.73; N,17.24. Found: C,70.02; H,5.53; N,17.22.
N-[(2S,4R)-methyl-5-phenyl-2,4-dihydro-1H-imidazo[1,2-a][1,4]benzodiazepin-4-yl]-N'-[6-indolyl]-urea (21 mg total) was obtained in >99% diastereomeric purity: m.p. 190°–185° C.(d).
¹HNMR (CDCl₃): Consistent with structure and confirms solvate form;
HPLC: >98% pure at 214 nM;
FAB MS: 449(M⁺+H).
Elem. Anal. calc'd for $C_{27}H_{24}N_6O.0.4OEtOAc.0.65H_2O$: Calc'd: C,69.33; H,5.80; N,16.96. Found: C,69.27; H,5.47; N,16.98.

EXAMPLE 16

Preparation of (4S)-N-[(2S)-methyl-6-phenyl-2,4-dihydro-1H-imidazo [1,2-a][1,4]benzodiazepin4-yl]-(3-chlorophenyl)-1-acetamide and (4R)-N-[(2S)-methyl-6-phenyl-2,4-dihydro-1H-imidazo[1,2-a][1,4]benzodiazepin-4-yl]-(3-chlorophenyl)- 1-acetamide (4R,4S)-Amino-(2S)-methyl-6-phenyl-2,4-dihydro-1H-imidazo [1,2-a][1,4]benzodiazepine (74 mg, 0.25 mmole), prepared according to Example 15, Step C, was combined with 48 mg (0.28 mmole) 3-chlorophenylacetic acid, 38 mg (0.28 mmole) 1-hydroxybenzotriazole hydrate, 54 mg (0.28 mmole) 1-ethyl-3-(3-dimethylaminopropyl)carbodiimide hydrochloride (54 mg, (0.28 mmole), and 39 μL of triethylamine in 3 ml of N,N-dimethyl-formamide. The reaction mixture was stirred for 18 hours and concentrated. The residue was partitioned between ethyl acetate and water. The organic phase was separated, washed with brine and dried. Concentration of the combined organic extracts yielded 60 mg of crude product. Purification to homogeneity of the product mixture was accomplished via HPLC employing a Rexchrom Pirkle Covalent L-Leucine column (5μ, 100A). (Chromatography conditions: 1:1 hexane-isopropanol eluant containing 0.2% triethylamine; 2 ml/min flow rate). In this way, (4S)-N-[(2S)-methyl-6-phenyl-2,4-dihydro-1H-imidazo[1,2-a][1,4]benzodiazepin-4-yl]-(3-chlorophenyl)-1-acetamide was obained in excess of 99% diastereomeric purity: m.p. 116°–118° C.(d).
¹HNMR (CDCl₃): Consistent with structure and confirms solvate form;
HPLC: >99% chemically pure at 254 nM; $R_f$=0.59 (chloroform-methanol, 95:5)
FAB MS: 443(M⁺+H);
Elem. Anal. calc'd for $C_{26}H_{23}ClN_4O.0.2CHCl_3.0.4H_2O$: Calc'd: C,66.39; H,5.10; N,11.82. Found: C,66.42; H,5.11; N, 11.72.
(4R)-N-[(2S)-methyl-6-phenyl-2,4-dihydro-1H-imidazo[1,2-a][1,4]benzodiazepin-4-yl]-(3-chlorophenyl)-1-acetamide was obtained in 99% diastereomeric purity: m.p. 120°–124° C.(d).
¹HNMR (CDCl₃): Consistent with structure and confirms solvate form;
HPLC: >99% pure at 254 nM; $R_f$=0.53 (chloroform-methanol, 95:5)
FAB MS: 443(M⁺+H);
Elem. Anal. calc'd for $C_{26}H_{23}ClN_4O.0.15CHCl_3.0.3H_2O$: Calc'd: C,67.36; H,5.13; N,12.02. Found: C,67.37; H,5.13; N,11.97.

EXAMPLE 17

Preparation of (4S)-N-[(2S)-methyl-6-phenyl-2,4-dihydro-1H-imidazo [1,2-a][1,4]benzodiazepin-4-yl]-(6-indolyl)-1-acetamide and (4R)-N-[(2S)-methyl-6-phenyl-2,4-dihydro-1H-imidazo[1,2-a][1.4]benzodiazepin-4-yl]-(6-indolyl)-1-acetamide (4R,4S)-Amino-(2S)-methyl-6-phenyl-2,4-dihydro-1H-imidazo [1,2-a][1,4]benzodiazepine (78 mg, 0.269 mmole), prepared according to Example 15, Step C, was combined with 6-indolylacetic acid (61 mg (0.35 mmole), 1-hydroxybenzotriazole hydrate, 47 mg (0.35 mmole) 1-ethyl-3-(3-dimethylaminopropyl)carbodiimide hydrochloride (67 mg, (0.35 mmole), and 0.35 mmole of triethylamine in 6 ml of N,N-dimethylformamide. The pH of the reaction mixture was adjusted to 8.5 with triethylamine and stirring was continued for 2 hours. The reaction mixture was concentrated and the residue was partitioned between ethyl acetate and water. The organic phase was separated, washed with brine and dried. Concentration of the combined organic extracts yielded 190 mg of crude product. Purification of the product mixture initially by flash chromatography on silica gel (2–5% methanol in chloroform gradient) and then via HPLC employing a Rexchrom Pirkle Covalent L-Leucine column (5μ, 100A) (Chromatography conditions: 1:1 hexane-isopropanol eluant containing 0.2% triethylamine; 2 ml/min flow rate) provided (4S)-N-[(2S)-methyl-6-phenyl-2,4-dihydro-1H-imidazo[1,2-a][1,4]benzodiazepin-4-yl]-(6-indolyl)-1-acetamide in excess of 85% diastereomeric purity: m.p. 138°–140° C.(d).
¹HNMR (CDCl₃): Consistent with structure and confirms solvate form;
HPLC: >99% chemically pure at 214 nM;
FAB MS: 448(M⁺+H);
Elem. Anal. calc'd for $C_{28}H_{25}N_5O.0.3CHCl_3.0.15hexane$: Calc'd: C,70.66H,5.57; N,14.11. Found: C,70.92; H,5.48; N,14.11.
(4R)-N-[(2S)-methyl-6-phenyl-2,4-dihydro-1H-imidazo[1,2-a][1,4]benzodiazepin-4-yl]-(6-indolyl)-1-acetamide was obtained in 90% diastereomeric purity: m.p. 148°–150° C.(d).
¹HNMR (CDCl₃): Consistent with structure and confirms solvate form;
HPLC: >95% pure at 254 nM;
FAB MS: 448(M⁺+H);
Elem. Anal. calc'd for $C_{28}H_{25}N_5O.0.55CHCl_3$: Calc'd: C,66.81; H,5.02; N,13.65. Found: C,66.56; H,5.05; N,13.60.

What is claimed is:

1. A compound of structural formula:

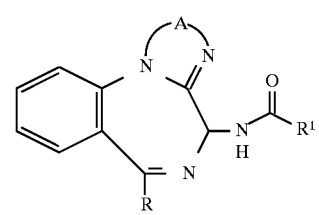

or a pharmaceutically acceptable salt thereof, wherein

R is
1) phenyl, either unsubstituted or substituted with chloro, bromo or fluoro, or $C_{1-3}$ alkyl or,
2) $C_{5-6}$ cycloalkyl;

A is
$C_{2-3}$ straight chain alkylene or alkenylene substituted with $C_{1-3}$ alkyl, or

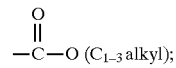

and

R[1] is
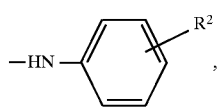
or
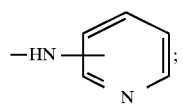
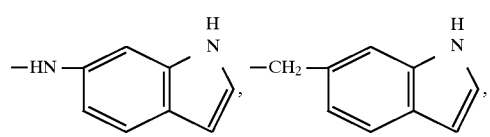
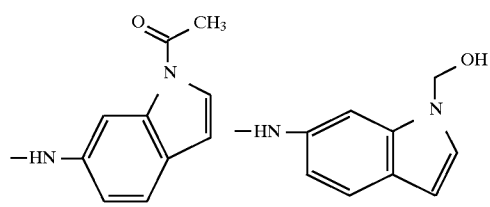
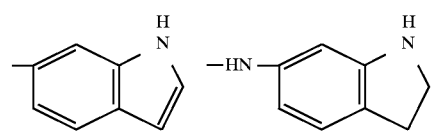
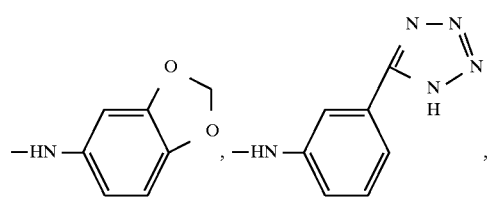
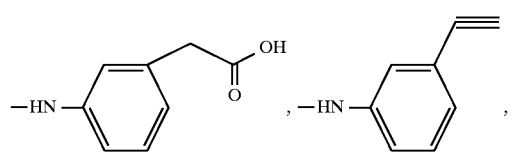
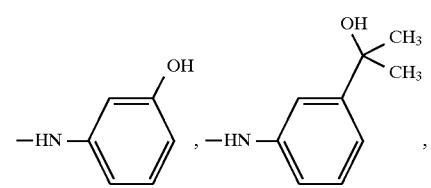
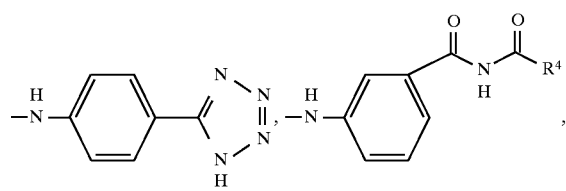
-continued
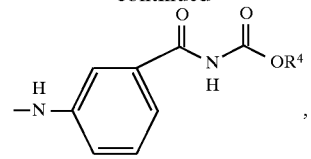
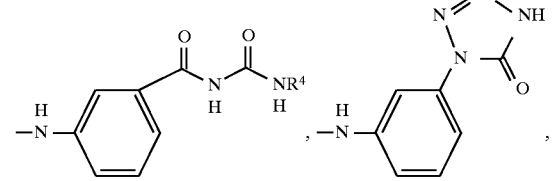
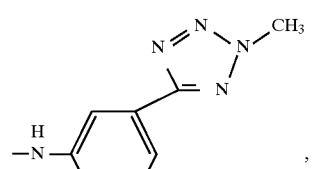
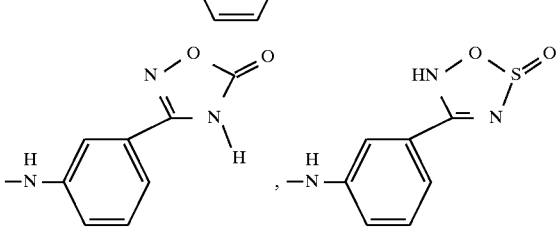
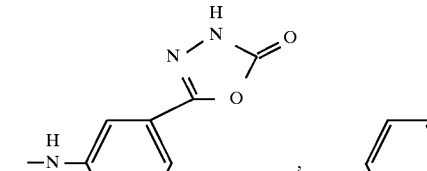
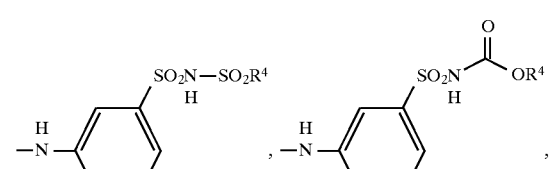
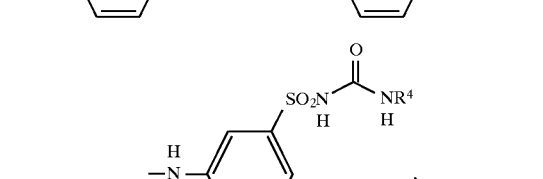
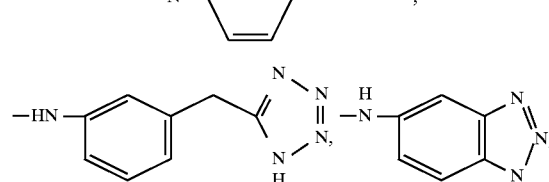
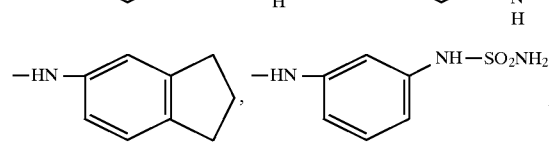

-continued

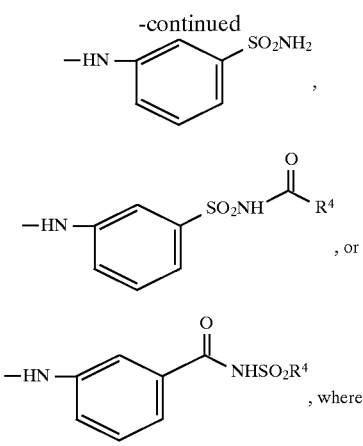

, or

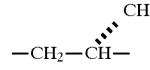

, wherein $R^4$ is $C_{1-6}$ alkyl, $CF_3$, cyclopropyl, 2,2-dimethylcyclopropyl, 2,2-di-fluorocyclopropyl, cyclobutyl, cyclopentyl, cyclohexyl, phenyl, or mono- or di-substituted phenyl wherein the substitution is F, Cl, Br, CN, $NO_2$, $CF_3$, $OCH_3$, or $NH_2$.

2. The compound of claim 1, wherein $R^1$ is

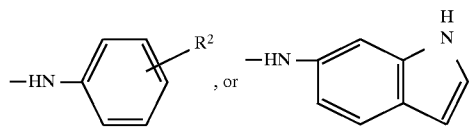

, or

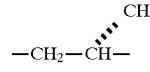

and R is phenyl or cyclohexyl.

3. The compound of claim 2 selected from the group consisting of those depicted in the following table:

| A | R | $R^2$ |
|---|---|---|
| —CH$_2$—CH(CH$_3$)— | phenyl | 3-CH$_3$— |
| —CH$_2$—CH(CH$_3$)— | phenyl | 3-CH$_3$— |
| —CH$_2$—CH(CH$_3$)— | cyclohexyl | 3-CH$_3$— |
| CH$_3$—CH—CH$_2$— | phenyl | 3-CH$_3$— |
| —CH$_2$—CH(CH$_3$)— | phenyl | 4-Cl— |
| —CH$_2$—CH(CH$_3$)— | phenyl | 3-Cl— |
| —CH$_2$—CH(CH$_3$)— | phenyl | 4-CF$_3$— |
| —CH—CH(CH$_3$)— | phenyl | 3-CH$_3$— |
| CH$_3$—CH—CH$_2$ | phenyl | 3-CH$_3$— |
| —CH$_2$—C(H)(C(O)OCH$_3$)— | phenyl | 3-CH$_3$— |
| CH$_3$—CH—CH— | phenyl | 3-CH$_3$—. |

4. The compound of claim 2 selected from the group consisting of those depicted in the following table:

| A | R | $R^1$ |
|---|---|---|
| —CH$_2$—CH(CH$_3$)— | phenyl | —HN—(3-CH$_3$-phenyl) |
| —CH$_2$—CH(CH$_3$)— | cyclohexyl | —HN-(indolyl) |

5. A pharmaceutical formulation comprising a pharmaceutically acceptable carrier and an effective amount of the compound of claim 1.

6. A method of antagonizing the binding of cholecystokinins to cholecystokinin receptors in a patient in need of such treatment which comprises the administration of an effective amount of the compound of claim 1.

* * * * *